United States Patent [19]

Abild

[11] 4,453,536
[45] Jun. 12, 1984

[54] BODY CHANNEL OCCLUDER

[76] Inventor: Robert N. Abild, 79 Vibberts Ave., New Britain, Conn. 06051

[21] Appl. No.: 203,438

[22] Filed: Nov. 3, 1980

[51] Int. Cl.³ .............................................. A61B 17/00
[52] U.S. Cl. .................................... 128/1 R; 128/325; 128/346; 128/DIG. 25
[58] Field of Search ................ 128/DIG. 25, 346, 274, 128/321, 344, 1 R, 325; 251/9; 3/1

[56] References Cited

U.S. PATENT DOCUMENTS

| | | | |
|---|---|---|---|
| 3,868,957 | 3/1975 | Doddington | 128/346 |
| 3,996,937 | 12/1976 | Williams | 128/346 X |
| 4,122,856 | 10/1978 | Mosior et al. | 128/321 X |
| 4,167,952 | 9/1979 | Reinicke | 128/DIG. 25 X |

OTHER PUBLICATIONS

Nabatoff, "An Adjustable Spring Clamp (Serrefine) for Cardiovascular Surgery", *Annals of Surgery,* (8/1953).

*Primary Examiner*—Michael H. Thaler
*Attorney, Agent, or Firm*—David S. Fishman

[57] ABSTRACT

A device which can act as a manually operable valve to permit or to prevent flow of bodily fluids, particularly urine, within their normal channels. The device is surgically implanted completely inside the body to prevent infection. Pressure on a button under the skin permits flow, and release of the pressure terminates flow. This effect is caused by arms positioned on opposite sides of the flow channel which produce a clamping action.

28 Claims, 5 Drawing Figures

BODY CHANNEL OCCLUDER

BACKGROUND OF THE INVENTION

(1) Field of the Invention

The present invention relates to an implantable occluder which will regulate the flow or discharge of bodily fluids through a membraneous body channel when the normal physiological mechanisms to accomplish such regulation no longer function properly for any reason including impairment due to various conditions such as malformation or disease. The present invention is particularly useful in the regulation of urine discharge through the urethra of an incontinent person, or the regulation of discharge of waste material from the intestines of a person who has undergone a colostomy or ileostomy operation. Apparatus in accordance with the present invention contains a clamping device which is normally closed, so as to occlude the membraneous channel. The clamping device may be opened when desired to allow the passage of bodily fluids through the membraneous channel. To avoid injury to the tissues of the membraneous channel, the clamping action is produced by making a sharp local bend in the channel. This is analogous to occluding flow of a garden hose by bending it sharply.

(2) Description of the Prior Art

Various devices for regulating the discharge of bodily fluids are known in the prior art. These prior devices are specifically related to the drainage of urine from the bladder of an incontinent person. A valve actuatable by lateral compression is disclosed in U.S. Pat. No. 3,758,073. As disclosed in this patent the valve is inserted directly into the urethra and normally is in a closed position. The valve may be opened by applying lateral pressure to the valve body. A principal disadvantage of devices of the type disclosed in U.S. Pat. No. 3,758,073 is that the urethra must be cut to insert the valve. This requires extensive surgery and may, in time, result in separation of the valve body and the urethra. Secondly, if adjustments are required additional operations are needed.

Another prior art device for controlling bodily drainage, attributed to Heyer Schute and known as a Rosen Inflatable Urinary Incontinence Prosthesis, contains two parallel arms opposing and a single arm carrying an inflatable balloon. The urethra is positioned between the balloon and the two parallel arms. When the balloon is fully inflated the urethra is occluded. The balloon is customarily filled with a saline solution, which is pumped into the balloon from a compressible reservoir bulb. The bulb contains a valve which can be opened, by manual pressure, to allow the saline solution to flow back into the bulb to thereby deflate the balloon. This system also presents various disadvantages. First, the urethra may not be fully occluded if the user fails to discharge the necessary amount of saline solution into the balloon. Secondly, the only method of properly adjusting the device is by the addition or subtraction of saline solution which is a cumbersome task. If the valve of the reservoir bulb fails the device must be replaced. Also the tubing connecting the several components can become kinked, making the unit inoperable.

While there are, in the prior art, valve type devices which would be useful in regulating the discharge from the intestines of a person who has undergone a colostomy operation, the above-discussed drainage control devices are limited for use only in conjunction with the urethra. There are no devices available in the prior art which may be used alternatively to control discharge from either the urethra or intestines.

SUMMARY OF THE PRESENT INVENTION

The present invention overcomes the above-discussed and other disadvantages and deficiencies of the prior art by acting on mechanical rather than hydraulic principles. Accordingly, devices in accordance with the present invention are not subject to long-term leakage or blockage problems.

A device in accordance with the present invention consists of a clamping assembly and an actuator assembly joined by a push-pull wire inside a conduit or sheath. The clamping assembly, in a preferred embodiment, has three arms, one of which can be moved closer to and farther from the other two arms. This movement may be accomplished by providing the moveable arm with a hinge or pivot about which it can be rotated. The position of the moveable arm is controlled by the push-pull wire from the actuator assembly.

The movement of the control wire is controlled by the actuator assembly which incorporates a push-button. The push-button is located under the skin but over the muscle, usually of the lower abdomen. A spring normally holds the button in a slightly raised position and the clamping assembly in a closed position. To drain body fluid the user merely presses on the skin area over the actuator button. This results in opening the clamp assembly through transmission of the buttom movement to the movable arm by the wire. To stop flow the user merely releases the actuator button, permitting the clamp to close.

Some of the objects of the present invention are to regulate the discharge of urine from the bladder of an incontinent person or to regulate discharge of bodily wastes from the intestines of a person who has undergone a colostomy or ileostomy operation.

BRIEF DESCRIPTION OF THE DRAWING

The present invention may be better understood, and its numerous advantages will be apparent to those skilled in the art, by reference to the accompanying drawings wherein like reference numerals refer to like elements in the several figures and in which.

DESCRIPTION OF THE PREFERRED EMBODIMENT

Figure 1:
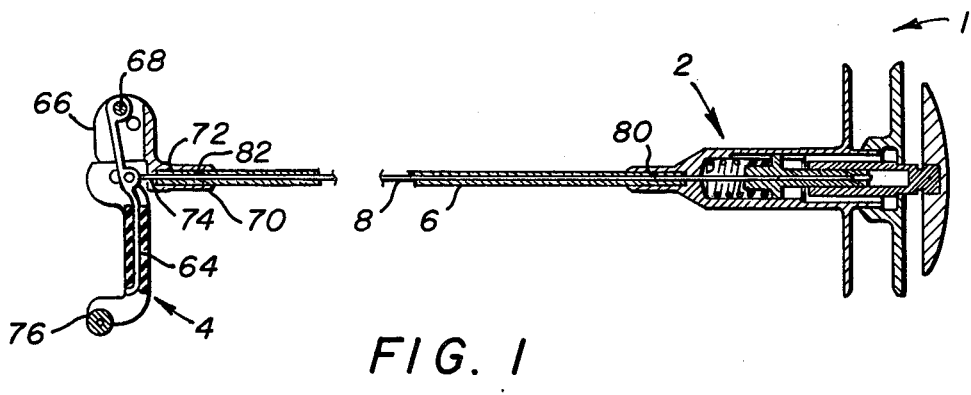
FIG. 1 is a cross-sectional side elevation view of a preferred embodiment of the present invention.

Referring to FIG. 1, an implantable occluder is generally indicated at 1. The implantable occluder 1 is comprised of a push-button type actuator sub-assembly 2 and a clamp sub-assembly 4. Actuator 2 is connected to clamp 4 by a flexible wire 8 which is enclosed in a flexible sheath 6. Wire 8 has a slightly longer length than sheath 6. The length of sheath 6 maintains a fixed positional relationship between clamping assembly 4 and actuating assembly 2.

Figure 2:
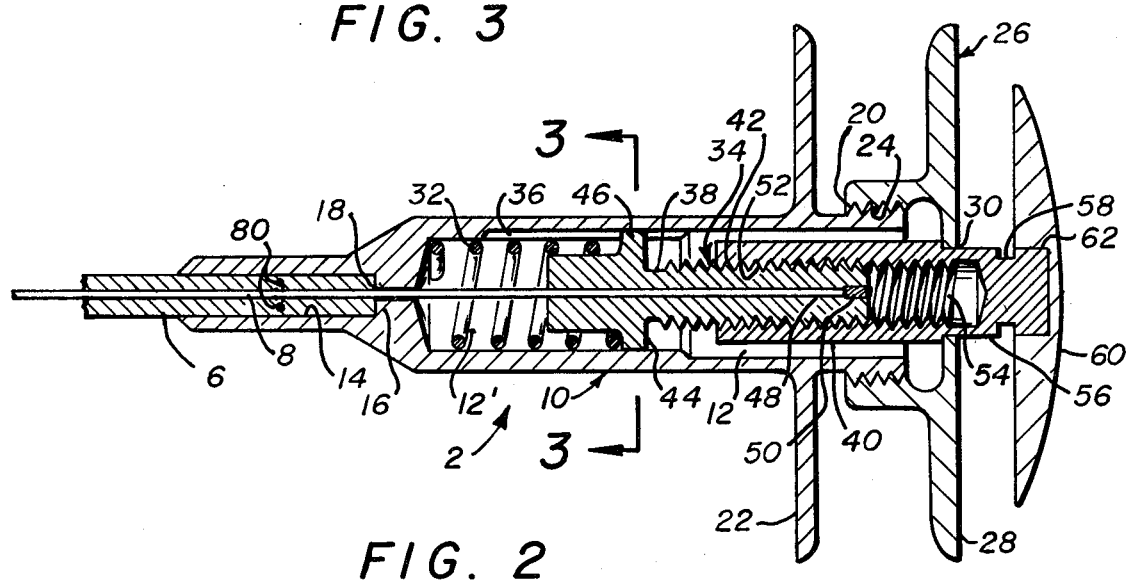
FIG. 2 is an enlarged sectional view of the actuator of the device of FIG. 1.

An enlarged view of the actuator sub-assembly 2 is presented in FIG. 2. Actuator 2 includes a push-button housing 10. Housing 10 is a tube-like structure with two chambers 12 and 14. Chamber 12 and chamber 14 are separated by collar 16 but are in communication with each other via passage 18. Chamber 14 has an inner diameter which is snug fit with the outer diameter of sheath 6. This allows the insertion of sheath 6 into chamber 14 at the first end of housing 10. Sheath 6 is inserted into chamber 14 until its end makes contact with a first side of collar 16. Passage 18 is of slightly larger diameter than wire 8. This allows easy passage of wire 8 from chamber 14 into chamber 12. A subchamber 12', which has a slightly reduced diameter when compared to the remainder of chamber 12, is provided at the end of chamber 12 adjacent chamber 14. A longitudinal groove 36 is provided within the wall of subchamber 12'; groove 36 extends inwardly from the larger diameter portion of chamber 12.

The outer surface of the second end of housing 10 is provided with a thread 20 and a radially outwardly extending flange 22. Thread 20 engages a complimentary thread 24 provided within a recessed first end of a separate end cap 26. There is a relief groove at the bottom of the recess in end cap 26. This permits cap 26 to be screwed down on housing 10 until the housing bottoms in the cap if necessary or desirable. As will be discussed below, the spacing of cap 26 from flange 22 will normally be determined by the thickness of the muscular wall through which the device is implanted. Cap 26 has an outwardly extending flange 28, which is generally parallel to flange 22 on housing 10, and an aperture 30 which is coaxial with chambers 12 and 14.

A biasing spring 32 is inserted into chamber 12 through the second end of housing 10 prior to installation of cap 26. Biasing spring 32 has a slightly smaller outside diameter than subchamber 12'. The first end of biasing spring 32 contacts collar 16.

An adjustment member 38 is provided, at its first end, with an external thread 42 and, near its second end, with a biasing spring engaging flange 44. Flange 44 is provided with spline 46 which fits within groove 36. This spline connection prevents the adjustment member 38 from rotating. Adjustment member 38 is also provided with a passage 48 which is coaxial with chambers 12, 12' and 14 and also with passage 18. Passage 48 is of a slightly larger diameter than wire 8. This allows wire 8 to be inserted into passage 48 from the second end of adjuster 38. Wire 8 is pushed through passage 48 so as to extend out past the first end of adjustment member 38. The first end of adjustment member 38 has a narrow transverse slot and a short internal threaded diameter. Wire 8 is secured into adjuster member 38 by bending its end by 90°, inserting it into the transverse slot and following it by small setscrew 50. A plunger member 34, in addition to the adjustment member 38, is inserted in chamber 12 prior to installation of cap 26. Plunger 34 includes a tubular extension 40.

Extension 40 of plunger 34 defines, at a first end, a chamber 54. Plunger extension 40 is provided with an internal thread 52. Thread 52 is complimentary to the thread 42 on the exterior of adjuster member 38 whereby the adjuster may be screwed into the plunger extension 40. Extension 40, at its second end, has a solid axially aligned prolongation 56. Prolongation 56 has a smaller diameter than aperture 30 in cap 28. This allows prolongation 56 to easily pass through aperture 30. Prolongation 56 is provided with a groove 58. Groove 58 has a width large enough to allow entry therein of the wall of cap 26 at aperture 30, if prolongation 56 of plunger 34 is pushed to one side.

Finally, actuator assembly 2 is provided with button 60. Button 60 may be of any shape, but preferably has a first side with a dome shape with the second side being flat. A blind hole 62 is provided within and coaxial with button 60. Hole 62 has a diameter slightly larger than that of prolongation 56. This allows prolongation 56 easy entry into hole 62. Extension 56 may be secured within hole 62 by any means such as by an adhesive or with a pin. The material of button 60 is a hard plastic or polymer. As finally assembled in the patient button 60 is normally held in a somewhat raised position under the skin by biasing spring 32.

Figure 3:
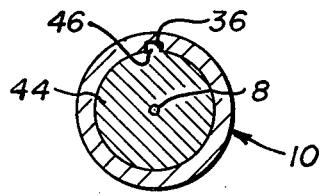
FIG. 3 is a sectional view taken along line 3—3 of FIG. 2.

Referring now to FIG. 3, a sectional view of actuator assembly 2 along line 3—3 of FIG. 2 is shown. FIG. 3 clearly shows the relationship of flange 44 and spline 46 of adjustment member 38 of plunger 34 to housing 10 and particularly to groove 36 in the housing. The materials from which plunger 34, adjustment member 38, housing 10 and cap 26 are made can be either stainless steel or a hard plastic or polymer such as Nylon or Teflon.

Figure 5:
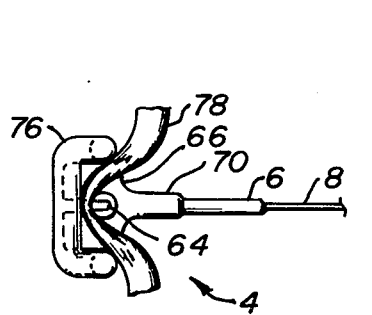
FIG. 5 is a side view of the clamp of FIG. 4.
Figure 4:
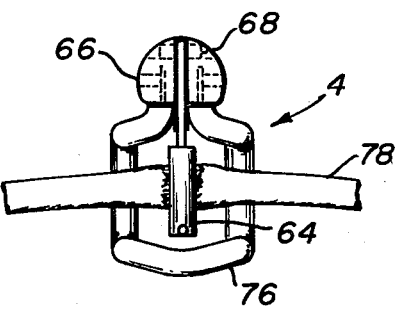
FIG. 4 is an end view, on an enlarged scale, of the clamp assembly of the FIG. 1 device.

FIGS. 4 and 5 are respectively end and side views of the clamp assembly 4. Clamp assembly 4, in the disclosed embodiment, is comprised of a pair of stationary arms 76 and a moveable arm 64. Stationary arms 76 may or may not be fastened as illustrated in FIGS. 4 and 5. Moveable arm 64 and stationary arms 76 are mounted in a clamp housing 66. Stationary arms 76 are secured within clamp housing 66 by any means, such as by providing housing 66 with holes to receive arms 76 and then securing the arm in these receiving holes by set screws or adhesive. Moveable arm 64 is pivotally supported on an axle 68. Axle 68 passes through housing 66 and arm 64. Arm 64 is able to turn on axle 68. A membraneous flow channel 78 of the patients body is placed between stationary arms 76 and moveable arm 64. Referring back to FIG. 1, clamp housing 66 is provided with a tubular extension 70. Clamp housing extension 70 defines a socket 72 having a diameter which will insure a slightly snug fit with the outer diameter of sheath 6. This allows sheath 6 to be inserted into socket 72 until the end of the sheath 6 makes contact with the bottom of the socket. A coaxial hole 74 is provided in the bottom of socket 72. Hole 74, which is coaxial with sheath 6, passes through housing 66 and is of a slightly larger diameter than wire 8. This allows wire 8 to pass through hole 74 and be connected, by a pin or other means, to moveable arm 64. The clamp assembly 4 may be made from stainless steel, with stationary arm 76 and moveable arm 64 covered with a silicone rubber where they contact the urethra.

The assembly outside the body of the implantable occluder 1 is as follows. The wire 8, which is enclosed in sheath 6, is inserted into socket 72 of housing extension 70 and the first end of wire 8 is then pushed through hole 72 and secured to moveable arm 64. Sheath 6 is secured in socket 72 by means of small wire pin 82 passed transversely through extension 70, socket 72 and sheath 6. The sheath 6 and wire 8 are inserted into chamber 14 of push-button housing 10, with the wire 8 being pushed through passage 18. Sheath 6 is secured in chamber 14 by means of small wire pin 80 passed transversely through housing 10, chamber 14 and sheath 6. Biasing spring 32 is inserted into subchamber 12' of push-button housing 10 and the adjuster 38 is then inserted in chamber 12. Wire 8 is pushed through passage 48 of adjustment member 38 and adjustment member 38 is rotated until spline 46 engages groove 36. Adjustment member 38 is then moved inwardly to compress biasing spring 32. Wire 8 is then moved so as to fully open implantable clamp assembly 4, and the second end of the wire 8 is then secured at the first end of adjustment member 38. While clamp assembly 4 is retained in an open position, tubular plunger extension 40 is screwed onto adjustment member 38.

The implantable occluder assembly as described above and without cap 26 or button 60 is ready to be implanted in the patient. A suitable incision is prepared in the patients crotch area or the abdominal wall. The occluder assembly is inserted through the incision. The clamping assembly is arranged at the membraneous urethra 78 with dual stationary arms 76 on one side of the urethra and moveable arm 64 on the other side thereof. The threaded portion 20 of the actuator assembly 2 is brought from inside to a circular aperture made in the muscular lower wall of the abdomen. Threaded portion 20 is passed from the inside through this aperture. Cap 26 is now separately inserted through an incision in the skin of the abdomen to one side of the location of actuator assembly. Cap 26 is secured onto the protruding threaded portion 20 of the actuator assembly 2. Flanges 22 and 28 have holes for sutures. These are now sutured to the abdomen wall to prevent turning. The clamping assembly also has holes for suturing, and these are sutured to adjacent muscles to keep the clamping assembly 2 in place. Button 60 is now passed through the skin incision and joined to protrusion 56 of the actuator and secured by a retaining pin. The actuator button 60 is now rotated to close the clamping assembly moveable arm 64 to a position where it is judged to just occlude flow in the urethra. The incisions are now closed. The amount of occlusion can be adjusted at any subsequent time by use of a special wrench with two needles. The two needles are passed through the skin over button 60 and slightly into the button. The button can now be rotated in steps as needed to increase or to decrease the amount of occlusion. The unit can be retained for an extended period in the open position of the clamping assembly by pushing the button 60 to one side so as to engage the edge of hole 30 in groove 58. By moving the button in the opposite direction, disengaging the edge of hole 30 from notch, operation of the unit is returned to normal.

The present invention possesses many unique advantages. For example, it is a push-button type occluder which is implanted completely within the body to mechanically control or actuate a remote internal function. The actuating body of a device in accordance with the invention will typically be installed under the skin thereby preventing infection. Since the above-discussed device operates on mechanical principles, reliability is maximized and the need for repair in long term usage is minimized. The device may be latched open, or unlatched, at any time by either the patient or an attendant and the occlusion is adjustable at any time by the physician without surgery.

While a preferred embodiment has been shown and described, various modifications and substitutions may be made thereto without departing from the spirit and scope of the invention. Accordingly, it must be understood that the present invention has been described by way of illustration and not limitation.

What is claimed is:

1. An improved apparatus for controlling the flow of body fluids through a channel, said apparatus being implantable within the body of a user, said apparatus comprising:
   clamp means for occluding flow through a body channel, said clamp means having at least a first stationary arm and a movable arm, the channel through which flow is to be controlled being positionable between said stationary and movable arms;
   actuator means, said actuator means being implantable within a muscular wall of the user's body with a portion thereof being positioned under the user's skin;
   elongated connector means, said connector means having an aperture extending lengthwise therethrough, said connector means including an elongated flexible member positioned within said aperture, said flexible member being attached at its opposite ends to said clamp means movable arm and to said actuator means, said flexible member being axially movable in said aperture by operation of said actuator means, said flexible member acting on said clamp means movable arm so as to spatially displace said movable arm towards and away from said stationary arm to thereby selectively control flow through the channel; and
   means for adjusting said clamp means in position in the body of the user to adjust the amount of occlusion.

2. The apparatus of claim 1 wherein said clamp means comprises a support means, two stationary arms and said movable arm, said arms being supported from said support means.

3. The apparatus of claim 2 wherein said clamp means support means includes an axle, said movable arm being pivotally mounted on said axle.

4. The apparatus of claim 3 wherein said support means and said arms of said clamp means are comprised of stainless steel.

5. The apparatus of claim 4 wherein said stationary and said movable arms are encased in silicon rubber.

6. The apparatus of claim 1 wherein said connector means further includes a flexible tubular sheath and wherein said elongated flexible member comprises a wire.

7. An improved apparatus for controlling the flow of body fluids through a channel, said apparatus being implantable within the body of a user, said apparatus comprising:
   clamp means for occluding flow through a body channel, said clamp means having at least a first stationary arm and a movable arm, the channel through which flow is to be controlled being positionable between said stationary and movable arms;
   actuator means, said actuator means being implantable within a muscular wall of the user's body with a portion thereof being positioned under the user's skin; and
   elongated connector means, said connector means having an aperture extending lengthwise therethrough, said connector means including an elongated flexible member positioned within said aperture, said flexible member being attached at its opposite ends to said clamp means movable arm and to said actuator means, said flexible member being axially movable in said aperture by operation of said actuator means, said flexible member acting on said clamp means movable arm so as to spatially displace said movable arm towards and away from said stationary arm to thereby selectively control flow through the channel, said actuator means comprising:

(a) housing means, said housing means having a tubular shape, said housing means having first and second second internal coaxial chambers, said first and said second chambers each having first and second ends, said first ends of said chambers being open to the exterior of said housing means and said second ends of said chambers being defined by a common dividing wall, said wall being provided with a passage having a smaller diameter than said chambers, a first end of said connector means being received within said first chamber, said connector means flexible member extending through said passage in said separator wall from said first chamber to said second chamber, said housing means being further provided with an outwardly extending radial flange adjacent to said first end of said second chamber, said housing means being implantable within a muscular wall of the user's body with said flange in contact with the inner side of the muscular wall;

(b) movable adjustor means, said adjustor means having a first and second ends, said adjustor means being received in said second chamber of said housing means with said first end thereof facing said dividing wall, said adjustor means having a protrusion extending outwardly therefrom to define a shoulder, said adjustor means having an aperture therein, said connector means flexible member extending into said aperture and being affixed to said adjustor means;

(c) resilient biasing means, said biasing means being positioned within said second chamber of said housing means, said biasing means extending between said dividing wall of said housing means and said adjustor means shoulder;

(d) cap means, said cap means having a tubular shape, said cap means having first and second ends, said second end of said cap means being open, said second end of said cap means being removably received on said housing means to cover said first end of said housing means second chamber, said first end of said cap means having an opening of a smaller diameter than said second end opening, said cap means first end opening being coaxial with said housing means chambers, said first end of said cap means being further provided with a radial protrusion, said protrusion being placed in contact with the outer side of the muscular wall upon implanting the apparatus;

(e) button means, said button means intended for positioning under the user's skin; and (f) means coupling said adjustor means second end to said button means, said coupling means extending through said cap means first end opening into said housing means second chamber whereby movements of said button means will be transmitted to said clamp means movable arm by said adjustor means and said connector means flexible member.

8. The apparatus of claim 7 wherein said second chamber of said housing means is provided with a subchamber adjacent said separating wall, said subchamber being of a smaller diameter than said second chamber.

9. The apparatus of claim 8 wherein said subchamber of said second chamber of said housing means is provided with an axial groove in the chamber defining wall.

10. The apparatus of claim 9 wherein said radial protrusion of said adjustor means is further provided with a spline which is received within said axial groove in the wall of said subchamber of said second chamber of said housing means.

11. The apparatus of claim 10 wherein said coupling means comprises:

a tubular extension of said adjustor means, said extension being threadably engaged with said adjustor means whereby a variable length plunger is defined, said tubular extension having an operating rod extending therefrom through said cap means to said button means.

12. The apparatus of claim 7 wherein said coupling means comprises:

a tubular extension of said adjustor means, said extension being threadably engaged with said adjustor means whereby a variable length plunger is defined, said tubular extension having an operating rod extending therefrom through said cap means to said button means.

13. The apparatus of claim 12 wherein said connector means further includes a flexible tubular sheath and wherein said flexible member comprises a wire, said tubular sheath being secured within said housing means first chamber.

14. The apparatus of claim 13 wherein said clamp means comprises two stationary arms.

15. The apparatus of claim 14 wherein said clamp means further comprises an axle, said movable arm being pivotally mounted on said axle.

16. The apparatus of claim 15 wherein said arms of said clamp means are comprised of stainless steel.

17. The apparatus of claim 16 wherein said stationary and said movable arms are encased in silicon rubber.

18. The apparatus of claim 17 wherein said cap means is threadably engaged with said housing means whereby said cap means is removable.

19. The apparatus of claim 15 wherein said tubular extension operating rod of said coupling means is provided with latch means, said latch means retaining said movable arm of said clamp means in a spatially displaced position from said stationary arm of said clamp means against the force of said biasing means by engaging the wall defining said opening in said first end of said cap means.

20. The apparatus of claim 19 wherein said latch means comprises a groove in said operating rod.

21. The apparatus of claim 15 wherein said clamp means is provided with a socket for receiving said connector means, said socket having an aperture for allowing said flexible member to be attached to said movable arm of said clamp means.

22. The apparatus of claim 21 wherein said connector means sheath is secured within said socket of said clamp means and is also secured within said first chamber of said actuator means housing means by pins.

23. An improved apparatus for controlling the flow of body fluids through a channel, said apparatus being implantable within the body of a user, said apparatus comprising:

clamp means for occluding flow through a body channel, said clamp means having at least a first stationary arm and a movable arm, the channel through which flow is to be controlled being positionable between said stationary and movable arms;

means for securing said clamp means in the body of the user;

actuator means, said actuator means being implantable within a muscular wall of the user's body with a portion thereof being positioned under the user's skin;

means for securing said actuator means in the body of the user;

elongated connector means, said connector means having an aperture extending lengthwise therethrough, said connector means including an elongated flexible member positioned within said aperture, said flexible member being attached to its opposite ends to said clamp means movable arm and to said actuator means, said flexible member being axially movable in said aperture by operation of said actuator means, said flexible member acting on said clamp means movable arm so as to spatially displace said movable arm towards and away from said stationary arm to thereby selectively control flow through the channel; and means for adjusting said clamp means in position in the body of the user to adjust the amount of occlusion after implantation in the body of the user.

24. The apparatus of claim 23 wherein said clamp means comprises a support means, two stationary arms and said movable arm, said arms being supported from said support means.

25. The apparatus of claim 24 wherein said clamp means support means includes an axle, said movable arm being pivotally mounted on said axle.

26. The apparatus of claim 25 wherein said support means and said arms of said clamp means are comprised of stainless steel.

27. The apparatus of claim 26 wherein said stationary and said movable arms are encased in silicon rubber.

28. The apparatus of claim 23 wherein said connector means further includes a flexible tubular sheath and wherein said elongated flexible member comprises a wire.

* * * * *